United States Patent [19]

Pourahmady

[11] Patent Number: 5,143,953
[45] Date of Patent: Sep. 1, 1992

[54] N-ALKYL MALEIMIDE THERMAL STABILIZERS FOR VINYL HALIDE POLYMERS

[75] Inventor: Naser Pourahmady, Avon Lake, Ohio

[73] Assignee: The B. F. Goodrich Company, Akron, Ohio

[21] Appl. No.: 635,042

[22] Filed: Dec. 28, 1990

[51] Int. Cl.$^5$ ............... C07D 207/27; C07D 207/267; C07D 405/04; C07K 5/3415
[52] U.S. Cl. ................................. 524/104; 524/105; 524/109; 524/111; 548/548; 548/549
[58] Field of Search ............... 524/104, 105, 111, 109; 525/282; 548/548, 549; 523/122; 252/403

[56] References Cited

U.S. PATENT DOCUMENTS

| | | | |
|---|---|---|---|
| 2,316,196 | 4/1943 | Tucker | 524/112 |
| 2,394,418 | 2/1946 | Quattlebaum et al. | 524/112 |
| 2,574,987 | 11/1957 | Shelley | 524/104 |
| 2,958,672 | 11/1960 | Goldberg | 525/282 |
| 3,105,059 | 9/1963 | der Burg et al. | 548/548 |
| 3,520,847 | 7/1970 | Runge et al. | 524/105 |
| 4,448,906 | 5/1984 | Deinet | 525/282 |

FOREIGN PATENT DOCUMENTS

| | | |
|---|---|---|
| 9007447 | 7/1990 | Egypt . |
| 0359464 | 3/1990 | European Pat. Off. . |
| 58-40374 | 3/1983 | Japan . |
| 1-16044 | 1/1989 | Japan . |
| 2-182741 | 7/1990 | Japan . |
| 47-41736 | 8/1990 | Japan . |
| 2-196845 | 8/1990 | Japan . |
| 6918756 | 6/1970 | Netherlands . |

OTHER PUBLICATIONS

The Condensed Chemical Dictionary-10th ed. pp. 31, 32 & 774 (1981), ed. G. G. Hawley, Van Nostrand Reinhold Co.

N-Substituted Maleimides as Thermal Stabilizers For Rigid Polyvinylchloride By M. W. Sabaa, M. G. Mikhael, N. A. Mohamed & A. A. Yassin which appeared in *Die Angewandte Makromolekulare Chemie* 168 (1989) 23-35 (Nr. 2718).

N-Substituted Maleimides As Thermal Stabilizers For Plasticized Poly(Vinyl Chloride) By Magdy W. Sabaa, M. G. Mikhael, N. A. Mohamed & A. Y. Yassin which appeared in *Polymer Degradation and Stability* 27 (1990) 319-336.

Dynamic Vulcanization of PVC-Epoxidized Natural Rubber Miscible Blend: The Effects of Dimaleimide Crosslinking By K. T. Varughese, P. P. De & S. K. Sanyal in *Die Angewandte Makromoleculare Chemie* 182 (1990) 73-83 (Nr. 3049, especially pp. 79-82.

*Primary Examiner*—Veronica P. Hoke
*Attorney, Agent, or Firm*—Miles B. Dearth; Joe A. Powell

[57] ABSTRACT

Thermal stability of vinyl halide polymers is enhanced by the use of dienophiles such as N-alkyl maleimides, and bis compounds thereof, disclosed herein. The maleimides and bis compounds thereof produce synergistic results in terms of thermal stability of vinyl halide polymers when used in conjunction with conventional metal-containing thermal stabilizers. Environmental concerns are abated and certain other advantages are realized if the maleimides disclosed herein are used in conjunction with conventional nonmetallic thermal stabilizers to stabilize vinyl halide polymers against heat deterioration. Bis compounds of the N-alkyl maleimides disclosed herein, when used as thermal stabilizers for vinyl halide polymers, promote crosslinking without degrading the vinyl halide polymer.

35 Claims, No Drawings

N-ALKYL MALEIMIDE THERMAL STABILIZERS FOR VINYL HALIDE POLYMERS

BACKGROUND OF THE INVENTION

Vinyl halide polymers, particularly polyvinyl chloride resins, are used in a variety of applications. These thermoplastic polymers can be fabricated into useful articles by extrusion, injection molding, compression molding and other thermoforming methods. Generally, these methods involve mixing the resins with certain additives to form compositions, heating the compositions to a temperature to fuse the resin particles, forming the compositions into the desired shape, and then cooling the composition to a solid. Due to the presence of unsaturation and labile allylic chlorines in the polymer backbone, the resins are sensitive to heat exposure and the resins are also sensitive to aging. The resins do not exhibit a distinct melting point and must be combined with fusing agents to facilitate their fusing during forming. At the temperatures that would be expected to melt the resins, the resins degrade and turn black. The polyvinyl chloride (PVC) resins degrade because the allylic chlorines are activated when exposed to heat and are released from the polymeric backbone. A free radical remains that then can react with another part of the backbone causing crosslinking, which renders such polymers unprocessable. Also, chlorine free radicals react together to form chlorine or with released hydrogen to form hydrogen chloride. Although PVC resins are initially white, thermoformed PVC articles that are damaged by heat during processing can range in color from yellow to black.

To stabilize vinyl halide polymers during thermoforming methods, heat or thermal stabilizers and cos-tabilizers are added to the resins. By using these stabilizers, the resin can be fused with a reduced degree of degradation and discoloration. Examples of known stabilizers include organometallic stabilizers, mixed metallic stabilizers, and inorganic stabilizers. Metallic stabilizers include heavy metal, alkali metal, and alkaline earth metal salts of fatty acids. The heavy metals include lead, cadmium, tin, and zinc. Popular organometallic stabilizers are dibutyltin maleate and dibutyltin di-2-ethylhexanoate. Examples of mixed metallic stabilizers include fatty acid salts of zinc and calcium, barium and cadmium, lead and barium, or two or more of other metals. Examples of inorganic stabilizers include lead carbonate, lead sulfate, and mixtures of tribasic lead sulfate and dibasic lead stearate. Examples of organic, non-metallic stabilizers or costabilizers include epoxidized soybean oil, tri(nonylphenyl) phosphite, $\beta$-aminocrotonates, $\beta$-diketones, and phenylindole.

One has only to observe the attempt to process a vinyl halide resin, such as resin, in the absence of any stabilizer to become a believer in the necessity for stabilization. Heating unstabilized PVC resin above its fusion point initially gives rise to yellowing, followed quickly by gross discoloration, evolution of hydrochloric acid, crosslinking, and ultimate charring to an infusible, unprocessable, corrosive black mass.

An article in *Die Angewandte Makromolekulare Chemie.* 168 (1989) 23-35 (Nr. 2718) discloses thermal stabilization of rigid PVC using maleimides. The article is by M. W. Sabaa, M. G. Mikhael, N. A. Mohamed, and A. A. Yassin of Cairo University and discloses fourteen aryl maleimides and one alkyl maleimide for thermal stabilization of rigid PVC. It is believed that this article leads away from consideration by those skilled in the art of N-alkyl maleimides as suitable stabilizers for rigid PVC because of poor performance of N-alkyl maleimides compared to the N-aryl maleimides that were tested. It is believed that the poor results obtained were due to the testing procedure employed in evaluating thermal stabilization, which testing procedure did not properly reflect the efficacy of the N-alkyl maleimide as a thermal stabilizer for rigid PVC.

SUMMARY OF THE INVENTION

Vinyl halide compositions or compounds containing 0.5-10 weight parts of one or more substituted or unsubstituted maleimide, or a bis compound thereof, per 100 weight parts of vinyl halide polymer or resin. Some of the maleimides which are excellent thermal stabilizers for PVC are new compounds. Maleimides together with at least one conventional metal-containing thermal stabilizer when incorporated in a vinyl halide polymer produce synergistic results in terms of thermal stabilization of the vinyl halide polymer. Vinyl halide polymers containing bis compounds of the maleimides crosslink through the bis compound to produce crosslinked vinyl halide polymers with improved physical properties.

OBJECTS OF THE INVENTION

It is an object of the present invention to replace or reduce the use of thermal stabilizers containing heavy metals with thermal stabilizers which are presently considered to be environmentally safe.

It is also an object of the present invention to replace the presently-used thermal stabilizers for vinyl halide polymers with dienophile stabilizers such as non-metallic N-alkyl maleimides.

It is also an object of this invention to use N-alkyl maleimide thermal stabilizers in vinyl halide resin formulations alone or in combination with at least one conventional stabilizer in order to obtain synergistic results in terms of thermal stabilization.

It is also an object of the present invention to use bis compounds of N-alkyl maleimides to thermally stabilize vinyl halide polymers whereby upon exposure to heat, the polymers crosslink but retain physical integrity and have improved tensile strength.

It is also an object of the present invention to protect as new compounds certain of the N-substituted maleimides disclosed herein which can thermally stabilize vinyl halide polymers.

These and other objects of this invention will become apparent from the description of the invention which follows.

DETAILED DESCRIPTION OF THE INVENTION

This invention pertains to vinyl halide compositions containing maleimide thermal stabilizers; to vinyl halide compositions containing N-substituted maleimide thermal stabilizers and conventional thermal stabilizers which contain or are devoid of a metal; vinyl halide compositions containing N-substituted maleimide thermal stabilizers and organic costabilizers; shaped articles from the compositions already noted made by extrusion, molding, or calendaring in the form of pipe, wire jacketing, siding, business machine components, sheet, and film; vinyl halide compositions containing bis compounds of N-substituted maleimides which crosslink but do not degrade upon processing; processes for preparing compositions noted above; and new N-substituted maleimide compounds which have the function of thermally stabilizing PVC.

The term "polymer" used herein includes homopolymers and copolymers. The vinyl halide homopolymers are polymers of a single principal vinyl halide monomer whereas copolymers are polymers of two or more comonomers. The term "N-substituted" includes straight and branched acyclic groups, cyclic groups, heterocyclic groups and alkaryl groups.

The vinyl halide polymers or resins are selected from polyvinyl halide, halogenated polyvinyl halide, and polyvinylidene halide. The vinyl halide polymers include homopolymers and copolymers. The vinyl halide copolymers contain at least 50 weight percent of at least one vinyl halide monomer and up to 50 weight percent, preferably up to 25 weight percent and especially up to 1% weight percent, of at least one suitable comonomer. Suitable comonomers which can be copolymerized with at least one vinyl halide monomer include: esters of vinyl alcohol containing 1 to 20 carbon atoms in the acid portion used to make the ester such as vinyl stearate, vinyl epoxystearate, vinyl benzoate, and vinyl acetate; acrylates and methacrylates containing 1 to 20, preferably 2 to 10 carbon atoms in the alcohol group used to make the ester such as ethyl acrylate, butyl acrylate, and 2-ethylhexyl acrylate; acrylonitrile, methacrylonitrile, and derivatives thereof; esters of unsaturated dicarboxylic acids such as maleates, fumarates, and itaconates; carbon monoxide; olefins containing 2 to 20, preferably 2 to 6 carbon atoms such as ethylene, propylene and isobutylene; diolefins containing 4 to 20, preferably 4 to 8 carbon atoms such as butadiene, isoprene and halogen derivatives thereof such as chloroprene; alkyl vinyl ethers such as vinyl isobutyl ether and cetyl vinyl ether; vinyl aromatics containing 8 to 30, preferably 8 to 16 carbon atoms such as styrene, alphamethyl styrene, and halogenated derivatives thereof such as para-chlorostyrene; vinyl organometallics such as monovinyldiethyl tin laurate, trialkyl tin acrylate and methacrylate, trialkylvinyl tin, unsaturated trihydrocarbon phosphate esters, vinyl phosphonic acid, N-chlorophthalimide, poly-N-allyl substituted aminotriazine, N-substituted maleimide, vinyl pyridine, and vinyl imidazone; alkenyl halides such as vinylidene chloride, vinyl bromide and fluoride, halogenated propenes, vinylidenechlorofluoride, and dichloroethylene; allyl glycidyl ether; allyl esters of hydroxyalkanoic acids; dimethyl dicrotonate; chloroalydene; isopropenyl chloride; tetrafluoroethylene; norbornene acrylate; (cyanoethoxy) ethyl acrylate; and isopropenyl acetate.

Preferred vinyl halide polymers include vinyl chloride, chlorinated vinyl chloride and vinylidene chloride homopolymers and copolymers. Preferred comonomers that may be copolymerized include the esters of acrylic acid such as methyl acrylate, ethyl acrylate, 2-hydroxyethyl acrylate, butyl acrylate, 2(2-ethoxyethoxy) ethyl acrylate, octyl acrylate, 2-ethylhexyl acrylate, and cyanoethyl acrylate; carbon monoxide; vinyl acetate; the esters of methacrylic acid such as methyl methacrylate, ethyl methacrylate, and butyl methacrylate; styrene and styrene derivatives including alpha-methyl styrene, vinyl toluene, and chlorostyrene; vinyl naphthalene; olefins such as ethylene, propylene, and isobutylene; diolefins such as butadiene, isoprene, and chloroprene; mixtures of any of these types of monomers and other unsaturated monomers copolymerizable therewith. The amount of comonomer(s) that can be polymerized with vinyl chloride is a function of the choice of comonomer(s), as is well understood by those skilled in the art.

The vinyl halide polymers described herein can be polymerized in any conventional manner such as dispersion, emulsion, mass, solution, condensation polymerization, and the like, with suspension being preferred. Generally, for the polymers produced using radical polymerization, polymerization is initiated with a free radical initiator such as an alkanoyl, aroyl, alkaroyl, or aralkanoyl diperoxide, a monohydroperoxide, or an azo compound, a peroxy ester, a percarbonate, or any other suitable free radical-type initiator. Examples of specific initiators include benzoyl peroxide, lauroyl peroxide, diacetyl peroxide, azobisisobutyronitrile, alpha, alpha'-azodiisobutyrate, 2,2'-azo-bis-(2,4-dimethyl valeronitrile), and the like. Polymerization can be carried out at suitable temperatures with temperatures of from about 0° C to 100° C. being suitable and from about 10° C. to about 85° C being preferred, and from about 40° to about 65° C. being especially preferred. The amount of the initiator utilized is generally quite small as from about 0.001 part by weight to about 1.0 part by weight and preferably from about 0.005 to about 0.1 part by weight for every 100 parts by weight of all the monomers being polymerized.

Molecular weight of the vinyl halide polymers, particularly vinyl chloride polymers, is measured in terms of inherent viscosity and is from about 0.3 to about 4, desirably from about 0.5 to about 2.5, and preferably from about 0.6 to about 2.2. The inherent viscosity is measured utilizing cyclohexanone as the solvent. The polymer is dissolved in the solvent at a concentration of 0.2 gram per 100 mls of cyclohexanone at 90° C. for 90 minutes and then the viscosity is measured with a viscometer in a water bath at 30° C. It is estimated that weight average molecular weight of the vinyl halide polymers described herein is generally in the range of 20,000 to 200,000. It is noted that in some instances, viscosity cannot be measured since the polymer will not fully dissolve.

The vinyl halide polymers are preferably not crosslinked so that they have good processing properties. In absence of bis maleimide thermal stabilizer noted herein, crosslinking of a vinyl halide polymer leads to an unprocessable, black solid polymer which has limited utility. However, it is to be understood that it is within the ambit of the present invention to either partially crosslink or fully crosslink the vinyl chloride polymers to provide improved physical properties. Should the vinyl chloride polymers be crosslinked or cured, any conventional crosslinking agent can be utilized such as diallyl phthalate, divinyl benzene, various diacrylates such as butanediol diacrylate, diethylene glycol diacrylate, and triacrylates such as trimethylolpropane triacrylate and trimethylolpropane trimethacrylate, and the like. Free radical initiators can also be used as crosslinkers herein. In presence of a bis maleimide thermal stabilizers, a reduced amount of a conventional crosslinker or no conventional crosslinker need be used since presence of a bis maleimide leads to crosslinked polymer without thermal degradation.

Vinyl halide polymers or resins prepared for rigid applications, generally contain less than about 30, preferably less than 10, weight parts of a plasticizer per 100 weight parts of the vinyl halide resin. Vinyl halide resins prepared for flexible applications contain greater than about 10 weight parts, preferably more than 30 weight parts and up to about 150 weight parts of a plasticizer per 100 weight parts of resin. In terms of Shore A hardness, rigid vinyl halide resins have hardness of greater than about 80, preferably greater than 90 whereas flexible vinyl halide resins have hardness of less than about 80.

Typical plasticizers include ester plasticizers such as dialkyl phthalates and the phosphate plasticizers such as tri(alkylphenyl) phosphates. The various plasticizers based on vegetable oils, such as epoxidized soybean oil, are costabilizers and are generally used with at least one stabilizer. Plasticizers based on other epoxidized vegetable oils are also used with various stabilizers as costabilizers to aid in their intended function.

As already noted, certain of the vinyl halide polymers which have a degree of flexibility contain a plasticizer. The known plasticizers are liquid. A thermal stabilizer can be incompatible with a rigid or flexible vinyl halide compound and an article made therefrom will not be transparent due to the incompatibility. This problem can be avoided by using a selected maleimide thermal stabilizer disclosed herein which is soluble in the liquid plasticizer. This can be done by initially dissolving the maleimide thermal stabilizer in a liquid plasticizer and then incorporating the plasticizer in the vinyl halide compound, along with other additives. In this manner, incompatibility is overcome and the article produced from plasticized vinyl halide polymer can be transparent.

The compositions or compounds of the present invention can contain conventional additives in conventional amounts. Thus, various conventional lubricants such as paraffin, polyethylene, and stearic acid; various processing aids such as polyacrylates; various other thermal stabilizers such as organometallics, mixed organometallics, and inorganics; various antioxidants such as BHT, which is butylated hydroxy anisole, other hindered phenols; various UV inhibitors such as substituted benzophenones; and the like, can be utilized.

Various fillers and pigments can also be utilized in conventional amounts such as up to about 700 parts by weight filler for every 100 parts by weight of vinyl chloride polymer. Examples of fillers include calcium carbonate, clay, silica, the various silicates, talc, carbon black, mica, and the like. Examples of pigments include titanium dioxide and carbon black, and many others to impart the desired color. Generally, the amount of such pigment is less than 30 weight parts per 100 weight parts of vinyl chloride polymer.

The various additives, fillers, pigments, and the like, are generally added and blended in a conventional manner. The compositions of the present invention can be mixed with the various additives in a mixer and then this powder compound can be processed on a two-roll mill into a sheet and cubed or the powder compound can be processed on an extruder into pellets or into a finished article. In general, any conventional compounding equipment such as a Banbury mixer, two-roll mill, extruder, injection molding machine, etc., can be used to produce the compositions of this invention.

The invention herein contemplates the use of at least one dienophile stabilizer selected from N-substituted maleimides. Suitable substituted maleimides as thermal stabilizers for vinyl halide polymers can generally be represented by the following structural formula I, which represents N-substituted maleimide, and structural formula II, which represents an N-substituted bis maleimide:

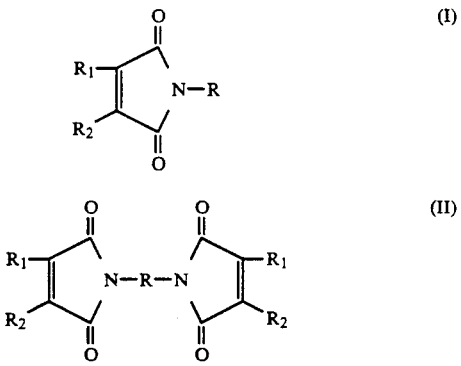

The maleimides represented above can be substituted or unsubstituted. The $R_1$ and/or $R_2$ substituents on the maleimide group can be hydrogens, alkyl groups of 1 to 12, preferably 1 to 6 carbon atoms or halides such as chloride or bromide atoms. Substituents on the R group, as used herein, are selected from hydrogens, alkyl groups of 1 to 12 but preferably 1 to 6 carbon atoms, halogen atoms such as chloride and/or bromide atoms, nitro groups, carboxy groups, hydroxyl groups, alkoxy groups of 1 to 6 carbon atoms, and mixtures thereof. Maleimide itself is not a suitable thermal stabilizer for vinyl halide polymers and, in fact, it is detrimental to vinyl chloride polymers in terms of thermal stability. R is the alkyl group.

Examples of suitable substituted maleimides herein include N-acyclic maleimides containing 1 to 30, preferably 1 to 18, and more preferably 1 to 10 carbon atoms in the acyclic group which can be alkyl, alkenyl and alkaryl group; N-cyclic maleimides containing 2 to 10, preferably 3 to 8 carbon atoms in the cyclic group; and N-alicyclic maleimides containing 3 to 32, preferably 4 to 26 carbon atoms in the alicyclic group which alicyclic group can be bonded to the nitrogen atom of the maleimide either via the cyclic structure or via the carbon atom of the side group. N-Alkoxyalkyl maleimides, which are part of the N-acyclic maleimides, containing 2 to 30, preferably 2 to 18 carbon atoms, in the alkoxyalkyl group and 1 to 4, preferably one oxygen in the alkoxy group; and N-heterocyclic or more preferably N-oxycyclic maleimides, which are part of N-cyclic maleimides, contain 2 to 10, preferably 3 to 6 carbon atoms and 1 to 2, preferably one oxygen in the oxycyclic ring. Aralkyl groups contain a pendant aryl group that are bonded to the nitrogen atom of the maleimide through a carbon atom in the alkyl group. Specific examples of N-substituted maleimides suitable herein include N-methyl maleimide, N-ethyl maleimide, N-isopropyl maleimide, N-amyl maleimide, N-dodecyl maleimide, N-octadecyl maleimide, N-benzyl maleimide, 1,4-bismaleimidocyclohexane, N-cyclohexyl maleimide, N-isopropoxypropyl maleimide, N-isopropoxypropyl citroconamide, and N-(2-tetrahydrofurfuryl) maleimide.

Some of the maleimides are available on the market and others can be made in a known manner using a two-step synthesis procedure. The first step is formation of amic acid at room temperature and the second step is cyclization which is carried out at an elevated temperature, such as 60° C. The synthesis generally involves the reaction of maleic anhydride and a corresponding primary amine. The bis compounds can be prepared in the same manner but the amine is a diamine.

Amount of the alkyl maleimides used for thermally stabilizing a vinyl halide polymer is 0.1 to 10, preferably 1 to 5 weight parts per 100 weight parts vinyl halide polymer.

The alkyl maleimide thermal stabilizers have advantages relating to crosslinking and aging. Self-crosslinking of vinyl halide polymer subjected to elevated temperature, as in an extruder, can be delayed by the use of an alkyl maleimide stabilizer. This is important since, although the bulk of the vinyl halide polymer in an extruder is continuously extruded, a small portion thereof remains in the extruder long after it is introduced into the extruder. If the remaining portion of the vinyl halide polymer is allowed to crosslink and thus degrade in terms of its color and processability, it will adversely affect the properties of the material being extruded since some of the degraded vinyl halide polymer will be comingled and extruded with the extrudate.

It has also been observed that extruded vinyl halide polymer articles have better aging characteristics when stabilized with an maleimide than a conventional thermal stabilizer. Tests have shown that after aging 7 days at 100° C., flexible PVC sheets of about 10-20 mils in thickness stabilized with an maleimide showed no crosslinking or brittleness as evidenced by loss in elongation compared to the same PVC sheet stabilized by the same amount of tribasic lead sulfate thermal stabilizer, which showed substantial decrease in elongation. Tribasic lead sulfate is one of the best thermal stabilizers against aging.

The bis compounds of maleimides disclosed herein have an unusual property as thermal stabilizers for vinyl halide polymers. The bis maleimides, when incorporated into a vinyl halide polymer, function as thermal stabilizers by retaining physical integrity of vinyl halide polymers or compounds even after crosslinking. This is unusual since normally, when thermal stabilizers other than the bis-maleimides are employed to stabilize vinyl halide polymers, the polymers become brittle and unprocessable upon self-crosslinking due to formation of pro-degradant by-products.

The maleimide thermal stabilizers noted herein can be used alone or together with conventional thermal stabilizers with a total amount of thermal stabilizers being 0.1 to 10, preferably 1-5 weight parts per 100 weight parts vinyl halide polymer. The alkyl maleimide stabilizers noted herein can be used in conjunction with conventional non-metal thermal stabilizers to synergistically stabilize against thermal degradation of vinyl halide polymers if a stabilizer package is desired which is devoid of a metal and which stabilizer package is safe to the environment. The use of non-metallic stabilizers in vinyl halide compounds is of special interest because of the environmental problems resulting from deposition of heavy metals by plastic wastes containing vinyl halide polymers. Examples of known or conventional non-metallic thermal stabilizers which can be combined with the maleimides noted herein include phosphite esters such as mixed, trisubstituted alkyl-aryl phosphites and epoxides such as epoxidized soybean oil. The phosphite ester stabilizers are generally used at a level of 0.1 to 3 weight part whereas epoxide stabilizers are generally used at a level of 1 to 7 weight parts per 100 weight parts of vinyl halide polymer. Such non-metallic thermal stabilizers consist of 10 to 90%, preferably 20 to 80% on weight basis, of at least one maleimide and remainder at least one non-metallic thermal stabilizer such as epoxidized soybean oil.

The maleimide stabilizers noted herein can also be used in conjunction with known or conventional metal-containing stabilizers in order to obtain synergistic results in terms of thermal stability of vinyl halide polymers. The conventional thermal stabilizers which contain at least one metal with which maleimides noted herein can be used in conjunction to produce synergistic results include organometallic, mixed metallic, and metal-containing inorganic thermal stabilizers. Examples of organometallic stabilizers include dibutyltin maleate and methyltin mercaptide. An organometallic stabilizer has a direct bond between a carbon and a metal. Examples of mixed metallic stabilizers include $C_2-C_{18}$ carboxylic acid salts of two or more metals selected from cadmium, barium, calcium, lead, and zinc. These mixed metallic stabilizers are complex mixtures of as few as two or as many as ten individual components. They consist, in general, of salts, soaps, bases, antioxidants, chelators, plasticizers, solvents, and diluents. Examples of inorganic thermal stabilizers which contain a metal include basic lead carbonate, disodium phosphate, trisodium phosphate, and lead sulfate. Amount of the alkyl maleimides in these mixed thermal stabilizers that produce synergistic results varies from 10 to 90%, preferably 20 to 80%, on weight basis, remainder being one or more of the conventional thermal stabilizers which contain metal.

Degradation of vinyl halide polymer, such as PVC, goes through evolution of hydrogen chloride, as evidenced by evolution of hydrogen chloride gas, formation of conjugated bonds, as evidenced by discoloration of PVC, crosslinking of PVC chains, as evidenced by brittleness and increased melt viscosity of PVC, and chain scission, which is evidenced by loss of physical properties when PVC becomes a black powder.

The maleimides are dienophiles and thus react with dienes formed in the chain of vinyl halide polymer during dehydrochlorination. The N-alkyl maleimides react with the dienes by means of Diels-Alder reaction at a possible crosslinking site. Thus, degradation of PVC through crosslinking and chain scission is stalled. Other dienophiles can be used together with one or more conventional metallic or nonmetallic heat stabilizers or mixtures thereof.

The following examples serve to illustrate the present invention with more particularity directed to the use of maleimides as thermal stabilizers in rigid and flexible vinyl halide compounds which are prepared with vinyl halide polymers and other components.

EXAMPLE 1

This example demonstrates the use of varying amounts and various maleimides as thermal stabilizers in vinyl chloride resin (PVC-1) which is a homopolymer of vinyl chloride prepared by suspension polymerization and having inherent viscosity (IV) of 1.0 and weight average molecular weight of about 200,000; and vinyl chloride suspension resin (PVC-2) which is a homopolymer of vinyl chloride with an IV of 0.5 and number average molecular weight of about 50,000.

Efficacy of the maleimide thermal stabilizers was evaluated by preparing PVC compounds and then evaluating the compounds on electrically heated Brabender mixer head for dynamic thermal stability (DTS) at 200° C. and 50 rpm. Initially, the maleimide was dissolved in plasticizer and the plasticizer, along with other additives, was incorporated by mixing with PVC-1 or PVC-2 vinyl halide resin to form the final vinyl chloride compounds. If no plasticizer was used, maleimide, and other additives, was mixed with the vinyl chloride resins. The color change was determined by taking samples every 2 minutes. Time to yellowing, time to dark, and time to torque increase were determined and the data therefor is tabulated in Table 1, below:

EXAMPLE 3

This example demonstrates efficacy of thermal stabilizer packages which are non-metallic and contain at last one N-alkyl maleimide disclosed herein and at least one conventional non-metallic thermal stabilizer.

TABLE 1

| COMPOUND INGREDIENTS | 1 | 2 | 3 | 4 | 5 | 6 | 7 | 8 | 9 | 10 | 11 | 12 |
|---|---|---|---|---|---|---|---|---|---|---|---|---|
| PVC-1 | — | 100 | 100 | — | 100 | 100 | 100 | 100 | 100 | 100 | 100 | 100 |
| PVC-2 | 100 | — | — | 100 | — | — | — | — | — | — | — | — |
| Plasticizer | — | 50 | 50 | — | 50 | 50 | 50 | 50[2] | 50 | 50 | 50 | 50 |
| Processing Aid | 1.0 | — | — | 1.0 | — | — | — | — | — | — | — | — |
| Lubricant | 0.8 | — | — | 0.8 | — | — | — | — | — | — | — | — |
| N-Methyl Maleimide | — | — | 3.0 | 3.0 | — | — | — | — | — | — | — | — |
| N-Dodecyl Maleimide | — | — | — | — | 1.6 | — | — | — | — | — | — | — |
| N-(Hydroxyethyl)Dimethyl Maleimide[5] | — | — | — | — | — | 3.0 | — | — | — | — | — | — |
| N-Cyclohexyl Maleimide | — | — | — | — | — | — | 1.5 | 2.0 | — | — | — | — |
| N-Ethyl Maleimide | — | — | — | — | — | — | — | — | 1.5 | — | — | — |
| N-Amyl-2-Methyl Maleimide[4] | — | — | — | — | — | — | — | — | — | 2.0 | — | — |
| N-Isopropoxypropyl Maleimide | — | — | — | — | — | — | — | — | — | — | 1.5 | — |
| N-(2-Tetrahydrofurfuryl) Maleimide | — | — | — | — | — | — | — | — | — | — | — | 1.8 |
| Initial Color | B | G | E | G | G | E[1] | E | G | G | G | E | G |
| Time to Yellow (Min.) | — | 6 | 20 | 14 | — | — | — | — | — | — | — | — |
| Time to Dark (Min.) | 8 | 13 | >60 | 34 | 10 | 14 | 32 | 16[1] | 34 | 10 | >60 | 32 |
| Min. Torque + 50% (Min.)[3] | 18 | 20 | >60 | 60 | 24 | 27 | >60 | 42[1] | >60 | >60 | >60 | >60 |

Initial Color Index—
E = excellent
G = good
F = fair
B = bad
[1]Performance evaluated with Brabender at temperature of 204° C. and 100 rpm.
[2]The plasticizer in this sample was diisodecyl phthalate whereas in all other samples the plasticizer was dioctyl phthalate.
[3]Minimum torque + 50% indicates commencement of degradation
[4]Also called N-amylcitraconamide

[5]Structural formula of this N-alkyl maleimide is 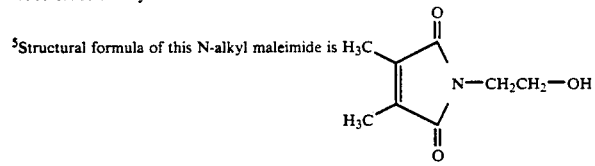

The data in Table 1 demonstrates efficacy of the maleimides as thermal stabilizers for rigid and flexible vinyl chloride resins.

EXAMPLE 2

This example demonstrates synergistic results when the maleimide thermal stabilizers disclosed herein are used in conjunction with conventional thermal stabilizer which contains a metal.

The samples herein were prepared as in the case of Example 1 and dynamic thermal stabilization was evaluated in a Brabender at a temperature of 200° C. and 50 rpm, as previously. The test results are summarized in Table 2, below:

The stabilizers were evaluated for dynamic thermal stability in vinyl chloride resin as in the previous examples and the data is summarized in Table 3, below:

TABLE 3

| | Formulation No. | | | | | | | |
|---|---|---|---|---|---|---|---|---|
| | 1 | 2 | 3 | 4 | 5 | 6 | 7 | 8 |
| PVC-1 | — | — | 100 | 100 | — | — | 100 | 100 |
| PVC-2 | 100 | 100 | — | — | 100 | 100 | — | — |
| DOP Plasticizer | — | — | 50 | 50 | — | — | 50 | 50 |
| Processing Aid | 1.0 | 1.0 | — | — | 1.0 | 1.0 | — | — |
| Wax Lubricant | 0.8 | 0.8 | — | — | 0.8 | 0.8 | — | — |
| N-Cyclohexyl-maleimide | — | 1.5 | — | 1.5 | — | 1.5 | — | 1.5 |

TABLE 2

| | FORMULATION NO. | | | | | | | | |
|---|---|---|---|---|---|---|---|---|---|
| | 1 | 2 | 3 | 4 | 5 | 6 | 7 | 8 | 9 |
| PVC-1 | 100 | 100 | 100 | 100 | 100 | 100 | 100 | 100 | 100 |
| DOP Plasticizer | 50 | 50 | 50 | 50 | 50 | 50 | 50 | 50 | 50 |
| N-Ethyl Maleimide | 1.0 (6 mmol) | 0.8 (4.5 mmol) | 0.5 (3 mmol) | 0.3 (1.5 mmol) | — | — | — | — | — |
| N-Cyclohexyl Maleimide | — | — | — | — | 1.2 (6 mmol) | 0.9 (4.5 mmol) | 0.6 (3 mmol) | 0.3 (1.5 mmol) | — |
| Barium/Cadmium Laurate | — | 0.8 (1.5 mmol) | 1.6 (3 mmol) | 2.4 (4.5 mmol) | — | 0.8 (1.5 mmol) | 1.6 (3 mmol) | 2.4 (4.5 mmol) | 3.2 (6 mmol) |
| Initial Color | G | E | E | E | E | E | E | E | E |
| Minutes to Yellow | 4 | 11 | 16 | 22 | 4 | 12 | 20 | 22 | 14 |
| Minutes to Dark | 20 | 13 | 20 | 32 | 26 | 16 | 23 | 30 | 17 |
| Minimum Torque + 50% | 30 | 20 | 22 | 32 | 40 | 20 | 26 | 32 | 20 |

TABLE 3-continued

| | Formulation No. | | | | | | | |
|---|---|---|---|---|---|---|---|---|
| | 1 | 2 | 3 | 4 | 5 | 6 | 7 | 8 |
| Phosphite Stabilizer* | — | — | — | — | 3.0 | 3.0 | 3.0 | 3.0 |
| Epoxidized Soybean Oil | 3.0 | 1.5 | 3.0 | 1.5 | — | — | — | — |
| Initial Color | F | G | E | E | F | F | G | G |
| Time to Dark (Min.) | 12 | 13 | 38 | >60 | 8 | 32 | 32 | 60 |
| Min. Torque + 50% (Min.) | 28 | 60 | >60 | >60 | 24 | 60 | 60 | >60 |

Initial Color Index -
E = excellent
G = good
F = fair
B = bad
*Ultranox 626

EXAMPLE 4

This example demonstrates the different physical properties that are obtained using N-alkyl maleimide alone as thermal stabilizer or together with a co-stabilizer. The compositions tested herein were typical wire and cable compound recipes where the resin was a vinyl chloride homopolymer, same as PVC-1 resin in Example 1, above. The N-alkyl maleimide thermal stabilizers tested herein included N-methyl maleimide and N-cyclohexyl maleimide. The co-stabilizer was epoxidized soybean oil.

The same evaluation procedure was used here as in Example 1 and the data is set forth in Table 4, below:

TABLE 4

| INGREDIENTS | LEAD STABILIZED | NON-LEAD I | NON-LEAD II |
|---|---|---|---|
| PVC Resin | 100.0 | 100.0 | 100.0 |
| DIDP[1] Plasticizer | 50.0 | 50.0 | 50.0 |
| Clay Filler | 10.0 | 10.0 | 10.0 |
| CaCO3 Filler | 10.0 | 10.0 | 10.0 |
| Wax Lubricant | 0.5 | 0.5 | 0.5 |
| Lead Stabilizer[2] | 5.5 | — | — |
| N-Methyl Maleimide | — | 4.0 | — |
| N-Cyclohexyl Maleimide | — | — | 5.0 |
| Epoxidized Soybean Oil | — | — | 3.0 |
| Thermal Properties | | | |
| Color of Extruded Sample | Good | Good | Good |
| Time to Torque Increase | >60 min. | >60 min. | >60 min. |
| Physical Properties | | | |
| Tensile Strength (psi) | | | |
| Prior to Aging | 3000 | 2892 | 2935 |
| Aged (7 days, 100° C.) | 2883 | 3108 | 2921 |
| % Change | −3.9 | +6.9 | −0.5 |
| % Elongation (at break) | | | |
| Prior to Aging | 237 | 210 | 307 |
| Aged (7 days, 100° C.) | 190 | 190 | 320 |
| % Change | −19.8 | −9.5 | +4.2 |

[1]DIDP represents diisododecyl phthalate
[2]Mixture of tribasic lead sulfate and dibasic lead stearate The results summarized in Table 4 above, demonstrate that lead stabilizer, a typical thermal stabilizer in wire and cable compound recipes, can be replaced with an N-alkyl maleimide thermal stabilizer without any loss of the physical properties such as tensile strength and elongation. The data in the above table also demonstrates that a metal-containing thermal stabilizer can be replaced with a novel non-metallic thermal stabilizer alone or together with a known non-metallic thermal stabilizer or co-stabilizer.

The results in Table 4 demonstrate that improved tensile strength can be obtained in a vinyl halide polymer stabilized with a lesser amount of N-methyl maleimide than lead stabilizer. Improved elongation at break can also be obtained if the PVC resin is stabilized with cyclohexyl maleimide and epoxidized soybean oil rather than the lead stabilizer.

EXAMPLE 5

This example demonstrates synergistic results obtained when N-cyclohexyl maleimide is used in conjunction with a nonmetallic stabilizer or costabilizer disodium phosphite to thermally stabilize vinyl halide polymer of Example 1, PVC-1, a homopolymer of vinyl chloride prepared by suspension polymerization and having IV of 1.0 and number average molecular weight of about 100,000.

The same evaluation procedure was used as in Example 1 with the exception that the Brabender was run at slightly higher load at 205° C. The data is set forth in Table 5, below:

TABLE 5

| | FORMULATION NUMBER | | | |
|---|---|---|---|---|
| Ingredients | 1 | 2 | 3 | 4 |
| PVC-1 | 100 | 100 | 100 | 100 |
| DOP Plasticizer | 50 | 50 | 50 | 50 |
| N-Cyclohexyl Maleimide | 1.2 (6 mmol) | 0.9 (4.5 mmol) | 0.3 (1.5 mmol) | — |
| Phosphite Stabilizer[1] | — | 0.5 (0.8 mmol) | 1.4 (2.3 mmol) | 1.8 (3 mmol) |
| Initial Color | G | G | E | E |
| Minutes to Dark | 12 | 20 | 35 | 33 |
| Minimum Torque + 50% | 20 | 25 | 36 | 33 |

[1]Ultranox 626

I claim:

1. A composition exhibiting improved dynamic thermal stability, wherein said compound comprises in the substantial absence of an added free radical generator a vinyl or vinylidene halide polymer, and a N-substituted maleimide containing one maleimide unit, said maleimide is selected from the group consisting of N-($C_1$ to $C_{12}$) maleimides, N-aralkyl maleimides having 1 to 12 carbon atoms in the N-alkyl portion, N-($C_4$ to $C_{26}$) cycloaliphatic maleimides, N-($C_2$ to $C_{30}$) oxyalkyl ether maleimides, and N-($C_2$ to $C_{10}$) oxyheterocyclic maleimides.

2. Composition of claim 1 wherein the amount of said maleimide is 1 to 5 weight part per 100 weight parts of said vinyl halide polymer, said maleimide is selected from N-methyl maleimide, N-ethyl maleimide, N-dodecylmaleimide, N-amyl maleimide, N-isopropoxypropyl maleimide, N-cyclohexyl maleimide, N-(2-tetrahydrofurfuryl) maleimide, mixtures thereof, and said vinyl halide polymer is selected from vinyl chloride homopolymers and copolymers, chlorinated vinyl chloride homopolymers and copolymers, vinylidene chloride homopolymers and copolymers, and mixtures thereof.

3. Composition of claim 2 further comprising a thermal stabilizer selected from:
   (a) organometallic stabilizers,
   (b) mixed metallic stabilizers,
   (c) inorganic stabilizers containing metal, and
   (d) mixtures thereof,
said thermal stabilizer imparts synergistic results to said vinyl halide polymer in terms of thermal stability.

4. Composition of claim 3 wherein said thermal stabilizer is selected from:
   (a) lead stabilizers,
   (b) barium-cadmium stabilizers,
   (c) calcium-zinc stabilizers,
   (d) barium-zinc stabilizers, and
   (e) mixtures thereof,
said thermal stabilizer imparts synergistic results to said vinyl halide polymer in terms of thermal stability.

5. Composition of claim 1 further comprising a co-stabilizer selected from:
   (a) epoxidized stabilizer,
   (b) phosphite stabilizers, and
   (c) mixtures thereof and said composition exhibits a synergistic stabilization effect.

6. Composition of claim 1 including at least 10 weights parts plasticizer per 100 weight parts of said vinyl halide polymer wherein said vinyl halide polymer is vinyl chloride polymer.

7. Process for improving the dynamic thermal stability of a vinyl halide polymer composition in the substantial absence of an added free radical generator comprising forming an intimate mixture of:
   (a) at least one vinyl halide polymer, and
   (b) an effective amount for thermally stabilizing said vinyl halide polymer of a thermal stabilizer comprising at least 0.1 weight parts of at least one N-substituted maleimide containing one maleimide unit selected from the group consisting of N-($C_1$ to $C_2$) maleimides, N-aralkyl maleimides having 1 to 12 carbon atoms in the N-alkyl portion, N-alicyclic maleimides, N-($C_2$ to $C_{30}$) oxyalkyl ether maleimides, and N-($C_2$ to $C_{10}$) oxyheterocyclic maleimides.

8. Process of claim 7, wherein said maleimide is selected from N-methyl maleimide, N-ethyl maleimide, N-dodecyl maleimide, N-amyl maleimide, N-isopropoxypropyl maleimide, N-cyclohexyl maleimide, N-(2-tetrahydrofurfuryl) maleimide, mixtures thereof, and thermal stabilizer mixtures containing at least one of the herein-enumerated maleimides; and said vinyl halide polymer is selected from vinyl chloride homopolymers and copolymers, chlorinated vinyl chloride homopolymers and copolymers, vinylidene chloride homopolymers and copolymers, and mixtures thereof.

9. Process of claim 7, wherein said thermal stabilizer contains 10–90%, on weight basis, of said at least one N-alkyl maleimide and remainder is selected from:
   (a) organometallic stabilizers,
   (b) mixed metallic stabilizers,
   (c) inorganic stabilizers containing metal, and
   (d) mixtures thereof,
said thermal stabilizer imparts synergistic results to said vinyl halide polymer in terms of thermal stability.

10. Process of claim 8 wherein said thermal stabilizer contains at least 10 to 90%, on weight basis, of said at least one N-alkyl maleimide and remainder is selected from
   (a) lead stabilizers,
   (b) barium-cadmium stabilizers,
   (c) calcium-zinc stabilizers,
   (d) barium-zinc stabilizers, and
   (e) mixtures thereof,
said thermal stabilizer imparts synergistic results to said vinyl halide polymer in terms of thermal stability.

11. Process of claim 7, wherein said at least one N-alkyl maleimide is the sole thermal stabilizer.

12. Process of claim 10 wherein vinyl halide polymer is selected from vinyl chloride homopolymers and copolymers, chlorinated vinyl chloride homopolymers and copolymers, vinylidene chloride homopolymers and copolymers, and mixtures thereof.

13. Process of claim 8 wherein said vinyl halide polymer composition contains at least 10 weight parts plasticizer per 100 weight parts of said vinyl halide polymer and wherein said vinyl halide polymer is vinyl chloride polymer.

14. Process of claim 7 wherein said thermal stabilizer is non-metallic.

15. Process of claim 8 wherein said thermal stabilizer contains 10 to 90%, on weight basis, of said at least one N-alkyl maleimide and remainder is selected from
   (a) epoxidized stabilizers,
   (b) phosphite stabilizers, and
   (c) mixtures thereof.

16. Process of claim 15 wherein said thermal stabilizer produces synergistic results in terms of thermal stability of said vinyl halide polymer and wherein said vinyl halide polymer is vinyl chloride polymer.

17. A shaped article comprising
   (a) at least one vinyl or vinylidene halide polymer,
   (b) an effective amount for thermally stabilizing said at least one vinyl halide polymer of a thermal stabilizer in the substantial absence of an added free radical generator, comprising at least 0.1 weight parts of at least one N-substituted maleimide containing one maleimide unit selected from the group consisting of N-($C_1$ to $C_{12}$) maleimides, N-aralkyl maleimides having 1 to 12 carbon atoms in the N-alkyl portion, N-($C_4$ to $C_{26}$) cycloaliphatic maleimides, N-($C_2$ to $C_{30}$) oxyalkyl ether maleimides, and N-($C_2$ to $C_{10}$) oxyheterocyclic maleimides.

18. Shaped article of claim 17 wherein said at least one N-ethyl maleimide is selected from N-methyl maleimide, N-ethyl maleimide, N-amyl maleimide, N-isopropoxypropyl maleimide, N-cyclohexyl maleimide, N-(2-tetrahydrofurfuryl) maleimide, mixtures thereof, and thermal stabilizer mixtures containing at least one of the herein-enumerated N-alkyl maleimides; and wherein said vinyl halide polymer is selected from vinyl chloride homopolymers and copolymers, chlorinated vinyl chloride homopolymers and copolymers, vinylidene chloride homopolymers and copolymers, and mixtures thereof.

19. Shaped article of claim 17 wherein said thermal stabilizer contains 10–90%, on weight basis, of said at least one N-alkyl maleimide and remainder is selected from:
   (a) organometallic stabilizers,
   (b) mixed metallic stabilizers,
   (c) inorganic stabilizers containing metal, and
   (d) mixtures thereof,
said thermal stabilizer imparts synergistic results to said vinyl halide polymer in terms of thermal stability.

20. Shaped article of claim 17 wherein said thermal stabilizer contains 10 to 90%, on weight basis, of said at least one N-alkyl maleimide and remainder is selected from
   (a) lead stabilizers,
   (b) barium-cadmium stabilizers,
   (c) calcium-zinc stabilizers,
   (d) barium-zinc stabilizers, and
   (e) mixtures thereof, said thermal stabilizer imparts synergistic results to said vinyl halide polymer in terms of thermal stability.

21. Shaped article of claim 18 wherein said at least one N-alkyl maleimide is the sole thermal stabilizer.

22. Shaped article of claim 17 wherein vinyl halide polymer is selected from vinyl chloride homopolymers and copolymers, chlorinated vinyl chloride homopolymers and copolymers, vinylidene chloride homopolymers and copolymers, and mixtures thereof.

23. Shaped article of claim 17 containing at least 10 weight parts of plasticizer per 100 weight parts of said vinyl halide polymer and said vinyl halide polymer is vinyl chloride polymer.

24. Shaped article of claim 17 devoid of plasticizer and wherein vinyl halide polymer is vinyl chloride polymer.

25. Shaped article of claim 17 wherein said thermal stabilizer is non-metallic.

26. Shaped article of claim 17 wherein said thermal stabilizer contains 10 to 90%, on weight basis, of at least one N-alkyl, maleimide and remainder is selected from
  (a) epoxidized stabilizers,
  (b) phosphite stabilizers, and
  (c) mixtures thereof.

27. Shaped articles of claim 26 wherein said thermal stabilizer produces synergistic results in terms of thermal stability of said vinyl halide polymer and wherein said vinyl halide polymer is vinyl chloride polymer.

28. Shaped article of claim 17 selected from extruded articles, molded articles, and calendared articles.

29. Shaped article of claim 17 selected from extruded articles, molded articles, and calendared articles.

30. Process of preparing a stabilizer composition for polyvinyl halide or polyvinyl halide comprising mixing in the substantial absence of an added free radical generator, 10%–90%, on weight basis, at least one N-substituted maleimide, wherein said maleimide is selected from the group consisting of N-($C_1$ to $C_{12}$) maleimides, N-aralkyl maleimides having 1 to 12 carbon atoms in the N-alkyl portion, N-($C_4$ to $C_{26}$) cycloaliphatic maleimides, N-($C_2$ to $C_{30}$) oxyalkyl ether maleimides, and N-($C_2$ to $C_{10}$) oxyheterocyclic maleimides, with remainder to 100% of at least one conventional stabilizer selected from metallic stabilizers, nonmetallic stabilizers, and mixtures thereof.

31. The process of claim 30 wherein said conventional stabilizer is selected from
  (a) organometallic stabilizers,
  (b) mixed metallic stabilizers,
  (c) inorganic stabilizers, and
  (d) mixtures thereof.

32. Process of claim 31 wherein said conventional stabilizer is selected from lead stabilizers, barium-cadmium stabilizers, calcium-zinc stabilizers, barium-zinc stabilizers, and mixtures thereof.

33. The process of claim 30 wherein said conventional stabilizer is selected from
  (a) epoxidized stabilizers,
  (b) phosphite stabilizers, and
  (c) mixtures thereof.

34. N-Isopropoxypropyl maleimide.

35. N-Isopropoxypropyl citraconamide.

* * * * *